(12) United States Patent
Imada et al.

(10) Patent No.: US 10,266,471 B2
(45) Date of Patent: Apr. 23, 2019

(54) PHENOLIC HYDROXYL-CONTAINING COMPOUND, COMPOSITION CONTAINING THE SAME, AND CURED FILM OF THE COMPOSITION

(71) Applicant: DIC Corporation, Tokyo (JP)

(72) Inventors: Tomoyuki Imada, Ichihara (JP); Norio Nagae, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 15/532,272

(22) PCT Filed: Nov. 19, 2015

(86) PCT No.: PCT/JP2015/082513
§ 371 (c)(1),
(2) Date: Jun. 1, 2017

(87) PCT Pub. No.: WO2016/114001
PCT Pub. Date: Jul. 21, 2016

(65) Prior Publication Data
US 2017/0334817 A1 Nov. 23, 2017

(30) Foreign Application Priority Data

Jan. 16, 2015 (JP) ................................ 2015-006725

(51) Int. Cl.
| | |
|---|---|
| *G03F 7/004* | (2006.01) |
| *G03F 7/11* | (2006.01) |
| *G03F 7/022* | (2006.01) |
| *C07C 39/14* | (2006.01) |
| *C08G 8/04* | (2006.01) |
| *C08G 65/40* | (2006.01) |
| *C09D 161/12* | (2006.01) |
| *C07C 39/17* | (2006.01) |
| *C08G 65/38* | (2006.01) |
| *G03F 7/039* | (2006.01) |
| *G03F 7/09* | (2006.01) |

(52) U.S. Cl.
CPC .............. *C07C 39/14* (2013.01); *C07C 39/17* (2013.01); *C08G 8/04* (2013.01); *C08G 65/38* (2013.01); *C09D 161/12* (2013.01); *G03F 7/0226* (2013.01); *G03F 7/039* (2013.01); *G03F 7/091* (2013.01); *G03F 7/094* (2013.01); *G03F 7/11* (2013.01); *C07C 2603/92* (2017.05)

(58) Field of Classification Search
None
See application file for complete search history.

(56) References Cited

U.S. PATENT DOCUMENTS

| | | | | |
|---|---|---|---|---|
| 9,828,457 | B2* | 11/2017 | Imada | G03F 7/0226 |
| 2012/0270157 | A1* | 10/2012 | Minegishi | G03F 7/09 430/323 |
| 2013/0078569 | A1* | 3/2013 | Jain | C07C 67/29 430/270.1 |
| 2015/0185613 | A1* | 7/2015 | Toyokawa | G03F 7/26 438/704 |
| 2016/0177020 | A1* | 6/2016 | Imada | C08G 8/28 430/270.1 |
| 2017/0066703 | A1* | 3/2017 | Imada | C07C 39/14 |
| 2017/0082923 | A1* | 3/2017 | Imada | G03F 7/023 |
| 2017/0329226 | A1* | 11/2017 | Imada | G03F 7/0392 |

FOREIGN PATENT DOCUMENTS

| | | | | |
|---|---|---|---|---|
| JP | 05-132543 | * | 5/1993 | |
| JP | 2010-248435 | A | 11/2010 | |
| JP | 2010-277061 | * | 12/2010 | |
| JP | 2012-162474 | * | 8/2012 | |
| JP | 2012-162474 | A | 8/2012 | |
| JP | 2012-252323 | A | 12/2012 | |
| JP | 2013-067697 | * | 4/2013 | |
| WO | 2014038680 | * | 3/2014 | |
| WO | 2015/008560 | * | 1/2015 | ................ G03F 7/11 |

OTHER PUBLICATIONS

Priority document JP 2013-150516 (filing date Jul. 2013).*
International Search Report dated Feb. 9, 2016, issued for PCT/JP2015/082513.

* cited by examiner

*Primary Examiner* — Martin J Angebranndt
(74) *Attorney, Agent, or Firm* — Locke Lord LLP

(57) ABSTRACT

A phenolic hydroxyl-containing compound is provided. The compound dissolves well in solvents and can be formulated into compositions that give coatings superior in thermal decomposition resistance, alkali developability, resolution, and dry-etch resistance. Specifically, the compound is a phenolic hydroxyl-containing calixarene represented by structural formula (1):

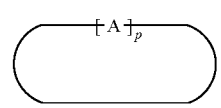

(1)

(where A is a structural unit including a dihydroxynaphthalene- or naphthol-derived structure optionally with a substituent alkyl, alkoxy, aryl, or aralkyl group or halogen atom on the aromatic rings and a methylene group optionally having an alkyl or aryl group in place of one of the hydrogen atoms) and obtained using a dihydroxynaphthalene in combination with a naphthol, with the total repeat number p being an integer of 2 to 10.

10 Claims, 3 Drawing Sheets

PHENOLIC HYDROXYL-CONTAINING COMPOUND, COMPOSITION CONTAINING THE SAME, AND CURED FILM OF THE COMPOSITION

TECHNICAL FIELD

The present invention relates to a phenolic hydroxyl-containing compound that dissolves well in solvents and can be suitably formulated into compositions that give coatings superior in thermal decomposition resistance, alkali developability, resolution, and dry-etch resistance. The present invention also relates to a composition for resists, a composition for bottom resist films, and a composition for permanent resist films, each composition containing the compound. Furthermore, the present invention relates to a resist coating, a bottom resist film, and a permanent resist film obtained using the composition for resists, the composition for bottom resist films, and the composition for permanent resist films, respectively.

BACKGROUND ART

Phenolic hydroxyl-containing compounds, used in adhesives, molding materials, paints, photoresist materials, raw materials for epoxy resins, curing agents for epoxy resins, etc., have also been utilized as the main ingredient of curable resin compositions and curatives for epoxy or other resins in various fields of electrical and electronics engineering, including semiconductor sealants and insulating materials for printed circuit boards, because of the superior characteristics they exhibit in the cured form, such as superb heat and moisture resistance.

One of such fields is photoresists. To be used as photoresists, not only should coatings be resistant to heat, they should have properties such as alkali solubility and light sensitivity. In the multilayer resist scheme, currently under active development as a method for the formation of more detailed wiring patterns than in the existing resist schemes, one or more layers called bottom resist film(s) or anti-reflective coating(s) are formed on a substrate, a resist pattern is formed on the layer(s) by conventional photolithography, and then dry etching is performed to transfer the wiring pattern to the substrate. An important component in the multilayer resist technology is the bottom resist film(s). The bottom film(s) needs to have, for example, high resistance to dry etching, low resist-pattern line edge roughness (LER), low optical reflection, and high resistance to thermal decomposition. The resin material for the bottom resist film(s), which is diluted in a medium prior to the formation of the film(s), needs to be soluble in commonly used organic solvents. Some modes of formation of the resist pattern require that the uncured resin composition for the bottom film(s) have certain performance characteristics, such as solubility in alkaline developers and the capability of being removed during the development of the photoresist.

Some known phenolic hydroxyl-containing compounds superior in heat resistance include a dihydroxynaphthalene novolac resin (see PTL 1) and a phenolic hydroxyl-containing compound that has the cylindrical structure called calixarene (see PTL 2). As for phenolic hydroxyl-containing compounds for bottom resist films, a known example is a fluorene-containing compound that has a molecular structure represented by the structural formula below (see PTL 3).

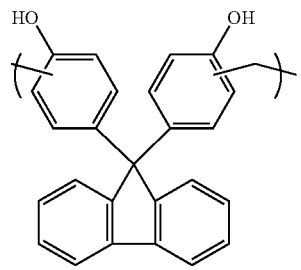

[Chem. 1]

Of these, the dihydroxynaphthalene novolac resin described in PTL 1 fails to achieve the required level of heat resistance, which has been increasingly high in recent years, although highly resistant to heat when compared with typical phenol novolac resins, and resists prepared therefrom are inferior in sensitivity and resolution. The 1-naphthol-based calix(4)arene described in PTL 2 is not sufficiently soluble in commonly used organic solvents and therefore are difficult to use in adhesive, paint, photoresist, and printed circuit board applications. The fluorene-containing compound described in PTL 3 is highly soluble in commonly used organic solvents and gives low optical reflection to coatings prepared by curing the compound, but does not meet the currently required level in terms of dry-etch and thermal decomposition resistance. There is a need to develop a phenolic compound for bottom resist films that combines higher dry-etch and thermal decomposition resistance.

CITATION LIST

Patent Literature

PTL 1: Japanese Unexamined Patent Application Publication No. 2010-248435
PTL 2: Japanese Unexamined Patent Application Publication No. 2012-162474
PTL 3: Japanese Unexamined Patent Application Publication No. 2012-252323

SUMMARY OF INVENTION

Technical Problem

An object of the present invention is therefore to provide a phenolic hydroxyl-containing compound that dissolves well in solvents and can be formulated into compositions that give coatings superior in thermal decomposition resistance, alkali developability, resolution, and dry-etch resistance. Another is to provide a composition that contains this phenolic hydroxyl-containing compound and can be suitably formed into bottom resist films and permanent resist films.

Solution to Problem

After extensive research to solve the above problem, the inventors have found, for example, that phenolic hydroxyl-containing compounds (calixarenes) obtained using a dihydroxynaphthalene in combination with a naphthol are significantly resistant to heat and highly soluble in commonly used solvents; and that coatings obtained using these compounds are superior in alkali developability, resolution, heat resistance, dry-etch resistance, and thermal decomposition resistance and therefore suitable for use as bottom resist films and permanent resist films. The present invention was completed on the basis of these findings.

That is, the present invention provides a phenolic hydroxyl-containing compound. The compound has a molecular structure represented by structural formula (1):

[Chem. 2]

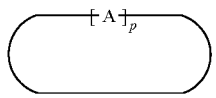
(1)

[where -A- is represented by structural formula (1-1) or (1-2):

[Chem. 3]

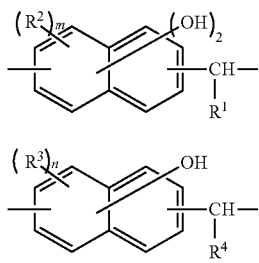

(where $R^1$ and $R^4$ are each hydrogen, alkyl, or aryl; $R^2$ and $R^3$ are each alkyl, alkoxy, aryl, aralkyl, or halogen; m is an integer of 0 to 4; if m is 2 or more, the plurality of $R^e$s may be the same or different from one another, and may be bonded to either of the two aromatic rings in the naphthylene structure; n is an integer of 0 to 5; and if n is 2 or more, the plurality of $R^a$s may be the same or different from one another, and may be bonded to either of the two aromatic rings in the naphthylene structure)]. The molecular structure includes two kinds of -A- units, one represented by (1-1) and the other by (1-2). The total number of repeats p of the units represented by (1-1) and (1-2) is an integer of 2 to 10.

The present invention also provides a photosensitive composition. This composition contains the above phenolic hydroxyl-containing compound and a photosensitizer.

The present invention also provides a composition for resists. This composition contains the above photosensitive composition.

The present invention also provides a resist coating. This resist coating is a coating of the above composition for resists.

The present invention also provides a curable composition. This composition contains the above phenolic hydroxyl-containing compound and a curing agent.

The present invention further provides a cured article. This article is a cured form of the above curable composition.

The present invention further provides a composition for bottom resist films. This composition contains the above curable composition.

The present invention further provides a bottom resist film. This bottom resist film is a film of the above composition for bottom resist films.

The present invention further provides a composition for permanent resist films. This composition contains the above curable composition.

The present invention further provides a permanent resist film. This permanent resist film is a film of the above composition for bottom resist films.

Advantageous Effects of Invention

The phenolic hydroxyl-containing compound according to the present invention dissolves well in solvents and can be suitably formulated into compositions that give coatings superior in thermal decomposition resistance, alkali developability, and dry-etch resistance. The composition can be suitably formed into positive resist films because of its superior heat resistance, alkali developability, and resolution. Coatings prepared from a curable composition containing a phenolic hydroxyl-containing compound according to the present invention are suitable for use as bottom resist films by virtue of its superior heat and dry-etch resistance and low optical reflection, and are also suitable for use as permanent resist films.

DESCRIPTION OF EMBODIMENTS

Figure 1:
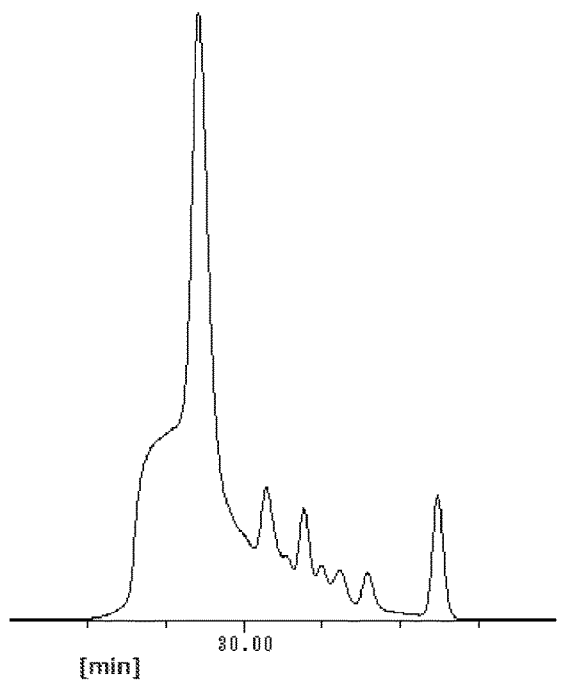
FIG. 1 is a GPC chart of phenolic hydroxyl-containing compound (1), obtained in Example 1.

A phenolic hydroxyl-containing compound according to the present invention has a molecular structure represented by structural formula (1):

[Chem. 4]

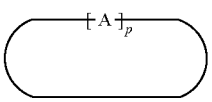
(1)

[where -A- is represented by structural formula (1-1) or (1-2):

[Chem. 5]

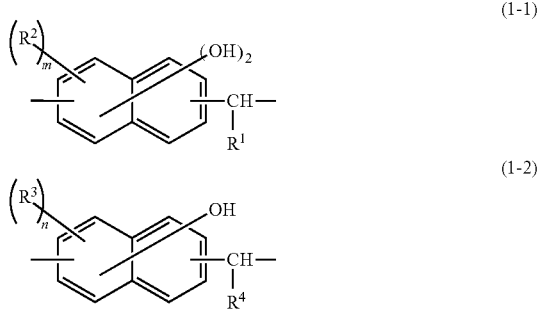

(1-1)

(1-2)

(where $R^1$ and $R^4$ are each hydrogen, alkyl, or aryl; $R^2$ and $R^3$ are each alkyl, alkoxy, aryl, aralkyl, or halogen; m is an integer of 0 to 4; if m is 2 or more, the plurality of $R^2$s may be the same or different from one another, and may be bonded to either of the two aromatic rings in the naphthylene structure; n is an integer of 0 to 5; and if n is 2 or more, the plurality of $R^a$s may be the same or different from one another, and may be bonded to either of the two aromatic rings in the naphthylene structure)]. The molecular structure includes two kinds of -A- units, one represented by (1-1) and the other by (1-2). The total number of repeats p of the units represented by (1-1) and (1-2) is an integer of 2 to 10.

As mentioned above, the known calixarenes are not sufficiently compatible with materials such as commonly used organic solvents, other resin components, and additives, although superior in thermal stability because of their high glass transition temperature and melting point. By contrast, the phenolic hydroxyl-containing compound according to the present invention has, in structural formula (1), a naphthylene unit with one hydroxyl group in combination with a naphthylene unit with two hydroxyl groups. Containing two naphthylene units with different numbers of hydroxyl groups, this compound is highly compatible with materials such as commonly used organic solvents, other resin components, and additives besides maintaining a high heat resistance characteristic of the calixarene structure.

The phenolic hydroxyl-containing compound according to the present invention gives superior light sensitivity and resolution to photosensitive materials made therewith. In positive resist applications, for example, resist coatings formed using this compound are highly sensitive to light and superior both in pre-exposure alkali resistance and post-exposure alkali solubility, allowing the manufacturer to produce detailed resist patterns.

The phenolic hydroxyl-containing compound according to the present invention, represented by structural formula (1), is very rigid by virtue of the calixarene structure containing multiple naphthalene rings. Bottom resist films made using this compound thus exhibit superior resistance to dry etching with etchants such as halogen plasma gases and to thermal decomposition. Furthermore, the high refractive index and absorbance originating in the many naphthalene rings lead to low optical reflection of cured articles, making this compound a suitable material for bottom resist films. The phenolic hydroxyl-containing compound according to the present invention, represented by structural formula (1), is also superior in thermal decomposition resistance, which makes this compound suitable for use as a material for permanent resist films, too.

The number p in structural formula (1) is the total number of repeats of the units represented by (1-1) and (1-2) and is an integer of 2 to 10. It is particularly preferred that the number p be 2, 3, 4, 5, 6, or 8, 4 in particular. This makes the phenolic hydroxyl-containing compound superior in structural stability and thermal decomposition resistance.

The phenolic hydroxyl-containing compound according to the present invention only needs to, as stated above, have the unit represented by (1-1) in combination with the unit represented by (1-2) with the total number of (repeats of) units represented by (1-1) and (1-2) between 2 and 10. This means that the phenolic hydroxyl-containing compound according to the present invention can have various numbers of units represented by (1-1) and (1-2) in various positions. Specifically, the units represented by (1-1) and (1-2) may exist randomly or in blocks. More specifically, the unit "-A-" in structural formula (1) can be, for example, a structure having any of the following sequences. In these sequences, "(1-1)" denotes structural formula (1-1), and "(1-2)" structural formula (1-2).

(1-1)-(1-2)
(1-1)-(1-1)-(1-2)
(1-2)-(1-2)-(1-1)
(1-1)-(1-2)-(1-2)
(1-2)-(1-1)-(1-2)
(1-1)-(1-2)-(1-1)-(1-2)
(1-1)-(1-1)-(1-2)-(1-2)
(1-1)-(1-1)-(1-1)-(1-2)
(1-1)-(1-2)-(1-2)-(1-1)

In structural formula (1-1), the two hydroxyl groups in the naphthylene structure may exist in either of the two aromatic rings of the naphthylene structure. Of the phenolic hydroxyl-containing compounds according to the present invention, particularly preferred ones have a structure in which the dihydroxylated naphthylene unit of structural formula (1-1) has the two hydroxyl groups in positions 1 and 4, 1 and 5, 1 and 6, 2 and 6, or 2 and 7. For such phenolic hydroxyl-containing compounds, a raw material (dinaphthol, described hereinafter) is readily available. More preferably, the two hydroxyl groups are in positions 1 and 6. This makes the production of the phenolic hydroxyl-containing compound according to the present invention easier than otherwise.

Of the phenolic hydroxyl-containing compounds according to the present invention, furthermore, particularly preferred ones have a structure in which the monohydroxylated naphthylene unit of structural formula (1-2) has the hydroxyl group in position 1. Such phenolic hydroxyl-containing compounds can be formed into coatings superior in thermal decomposition resistance.

That is, of the phenolic hydroxyl-containing compounds according to the present invention, particularly preferred ones have a structure in which the dihydroxylated naphthylene unit of structural formula (1-1) has the two hydroxyl groups in positions 1 and 4, 1 and 5, 1 and 6, 2 and 6, or 2 and 7 and in which the monohydroxylated naphthylene unit of structural formula (1-2) has the hydroxyl group in position 1, more preferably a structure in which the dihydroxylated naphthylene unit of structural formula (1-1) has the two hydroxyl groups in positions 1 and 6 and in which the monohydroxylated naphthylene unit of structural formula (1-2) has the hydroxyl group in position 1.

Specifically, phenolic hydroxyl-containing compounds having a structure in which the unit of structural formula (1-1) is one represented by structural formula (1-1-1) and the unit of structural formula (1-2) is one represented by structural formula (1-2-1) are more preferred than others.

[Chem. 6]

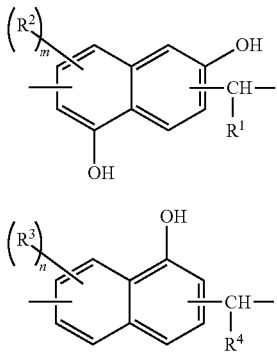

(In these formulae, $R^1$ and $R^4$ are each hydrogen, alkyl, or aryl, and p is an integer of 2 to 10; $R^2$ and $R^3$ are each alkyl, alkoxy, aryl, aralkyl, or halogen; m is an integer of 0 to 4; if m is 2 or more, the plurality of $R^2$s may be the same or different from one another, and may be bonded to either of the two aromatic rings in the naphthylene structure; n is an integer of 0 to 5; and if n is 2 or more, the plurality of $R^3$s may be the same or different from one another, and may be bonded to either of the two aromatic rings in the naphthylene structure.)

Of the phenolic hydroxyl-containing compounds according to the present invention, particularly preferred ones have a proportion of units of structural formula (1-1) to units of structural formula (1-2), as a molar ratio [structural formula (1-1):structural formula (1-2)], between 1:0.01 and 1:50 by reason of their coating properties and heat resistance when used as a resist material. More preferably, this proportion is between 1:0.05 and 1:20. This ensures intramolecular hydrogen bonds derived from the ring structure will work.

$R^1$ and $R^4$ in structural formulae (1-1) and (1-2) are each hydrogen, alkyl, or aryl. Examples of alkyls include methyl, ethyl, propyl, butyl, pentyl, hexyl, and cyclohexyl. Examples of aryls include structural portions represented by structural formula (2-1) or (2-2):

[Chem. 7]

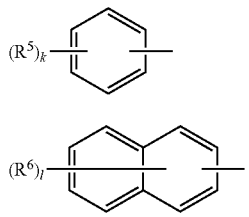

(where $R^5$ and $R^6$ are each independently hydroxyl, halogen, alkyl, alkoxy, aryl, or aralkyl, k is an integer of 0 to 5, and l is an integer of to 7; and if k or l is 2 or more, the plurality of $R^a$s or $R^4$s may be the same or different from one another). Specific examples of aryls include phenyl, hydroxyphenyl, dihydroxyphenyl, hydroxyalkoxyphenyl, alkoxyphenyl, tolyl, xylyl, naphthyl, hydroxynaphthyl, and dihydroxynaphthyl.

It is particularly preferred that $R^1$ and $R^4$ be aryl. This gives the photosensitive composition high sensitivity and resolution, and makes the phenolic hydroxyl-containing compound highly resistant to dry etching and thermal decomposition. $R^1$ and $R^4$ are more preferably hydroxyl-containing structural portions, such as hydroxyphenyl, dihydroxyphenyl, hydroxyalkoxyphenyl, hydroxynaphthyl, or dihydroxynaphthyl, even more preferably hydroxyphenyl.

$R^2$ and $R^3$ in structural formulae (1-1) and (1-2) are each alkyl, alkoxy, aryl, aralkyl, or halogen. Examples of alkyls include methyl, ethyl, propyl, butyl, pentyl, hexyl, and cyclohexyl. Examples of alkoxys include methoxy, ethoxy, propyloxy, butoxy, pentyloxy, hexyloxy, and cyclohexyloxy. Examples of aryls include phenyl, hydroxyphenyl, dihydroxyphenyl, hydroxyalkoxyphenyl, alkoxyphenyl, tolyl, xylyl, naphthyl, hydroxynaphthyl, and dihydroxynaphthyl. Examples of aralkyls include phenylmethyl, hydroxyphenylmethyl, dihydroxyphenylmethyl, tolylmethyl, xylylmethyl, naphthylmethyl, hydroxynaphthylmethyl, dihydroxynaphthylmethyl, phenylethyl, hydroxyphenylethyl, dihydroxyphenylethyl, tolylethyl, xylylethyl, naphthylethyl, hydroxynaphthylethyl, and dihydroxynaphthylethyl.

The value of m in structural formula (1-1) is preferably 0. This makes the phenolic hydroxyl-containing compound superior in thermal decomposition resistance. Likewise, the value of n in structural formula (1-2) is preferably 0. This makes the phenolic hydroxyl-containing compound superior in thermal decomposition resistance.

The phenolic hydroxyl-containing compound according to the present invention can be suitably produced by, for example, the methods below.

Method 1: Reacting a dihydroxynaphthalene and a naphthol with formaldehyde in the presence of a basic catalyst Method 2: Reacting a dihydroxynaphthalene and a naphthol with an aliphatic aldehyde compound having two or more carbon atoms or an aromatic aldehyde in the presence of an acidic catalyst In producing a phenolic hydroxyl-containing compound according to the present invention by method 1 or 2, the manufacturer can optionally modify reaction conditions to selectively obtain the phenolic hydroxyl-containing compound according to the present invention or to make a phenolic resin composition containing any other component. It is also possible to isolate the phenolic hydroxyl-containing compound from the phenolic resin composition containing any other component.

The dihydroxynaphthalene used in method 1 or 2 can be, for example, 1,4-dihydroxynaphthalene, 1,5-dihydroxynaphthalene, 1,6-dihydroxynaphthalene, 2,6-dihydroxynaphthalene, 2,7-dihydroxynaphthalene, or a derivative thereof whose aromatic nucleus is substituted with one or more alkyl and/or alkoxy groups. Examples of alkyls include methyl, ethyl, propyl, butyl, pentyl, hexyl, and cyclohexyl, and examples of alkoxys include methoxy, ethoxy, propyloxy, butoxy, pentyloxy, hexyloxy, and cyclohexyloxy. These may be used individually or in combinations of two or more.

Of these dihydroxynaphthalenes, 1,6-dihydroxynaphthalene and derivatives thereof whose aromatic nucleus is substituted with one or more alkyl and/or aralkyl groups are particularly preferred. With such a dihydroxynaphthalene, the manufacturer can produce the phenolic hydroxyl-containing compound efficiently. 1,6-Dihydroxynaphthalene is more preferred than derivatives.

The naphthol used in method 1 or 2 can be, for example, 1-naphthol, 2-naphthol, or a derivative thereof whose aromatic nucleus is substituted with one or more alkyl and/or alkoxy groups. Examples of alkyls include methyl, ethyl, propyl, butyl, pentyl, hexyl, and cyclohexyl, and examples of alkoxys include methoxy, ethoxy, propyloxy, butoxy, pentyloxy, hexyloxy, and cyclohexyloxy. These may be used individually or in combinations of two or more. 1-Naphthol is particularly preferred. It makes the phenolic hydroxyl-containing compound capable of giving coatings superior in thermal decomposition resistance.

The formaldehyde used in method 1 can be in the form of a solution, i.e., formalin, or a solid, i.e., paraformaldehyde.

The aliphatic aldehyde having two or more carbon atoms or aromatic aldehyde used in method 2 can be, for example, a compound represented by any of structural formulae (3-1) to (3-3):

[Chem. 8]

(3-1)

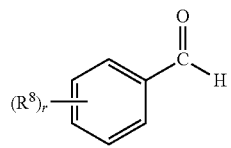
(3-2)

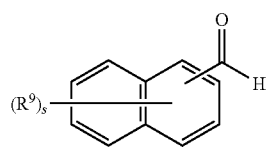
(3-3)

(where $R^7$ is a hydrocarbon having one to six carbon atoms or a structural portion resulting from replacing one or more carbon atoms in such a hydrocarbon with a hydroxyl, alkoxy, or aryl group or halogen atom; $R^8$ and $R^9$ are each independently hydroxyl, alkyl, alkoxy, aryl, aralkyl, or halogen, r is an integer of 0 to 5, and s is an integer of 0 to 7; if r or s is 2 or more, the plurality of $R^8$s or $R^9$s may be the same or different from one another).

Examples of aliphatic aldehydes represented by structural formula (3-1) include acetaldehyde, propylaldehyde, butylaldehyde, isobutylaldehyde, pentylaldehyde, and hexylaldehyde.

Examples of aromatic aldehydes represented by structural formula (3-2) or (3-3) include hydroxybenzaldehyde compounds such as salicylaldehyde, 3-hydroxybenzaldehyde, 4-hydroxybenzaldehyde, 2-hydroxy-4-methylbenzaldehyde, 2,4-dihydroxybenzaldehyde, and 3,4-dihydroxybenzaldehyde; hydroxy- and alkoxy-bearing benzaldehyde compounds such as 2-hydroxy-3-methoxybenzaldehyde, 3-hydroxy-4-methoxybenzaldehyde, 4-hydroxy-3-methoxybenzaldehyde, 3-ethoxy-4-hydroxybenzaldehyde, and 4-hydroxy-3,5-dimethoxybenzaldehyde; alkoxybenzaldehyde compounds such as methoxybenzaldehyde and ethoxybenzaldehyde; and hydroxynaphthaldehyde compounds such as 1-hydroxy-2-naphthaldehyde, 2-hydroxy-1-naphthaldehyde, and 6-hydroxy-2-naphthaldehyde. These aldehyde compounds may be used individually or in combinations of two or more.

Of the aldehydes used in method 2, aromatic aldehydes represented by structural formula (3-2) or (3-3) are particularly preferred. With any such aldehyde, the resulting phenolic hydroxyl-containing compound will be highly soluble in organic solvents and highly resistant to heat, and the photosensitive composition will be superior in sensitivity. In bottom resist film applications, furthermore, the coatings will be superior in dry-etch and thermal decomposition resistance. Compounds that have one or more hydroxyl or alkoxy groups substituting the aromatic ring(s) are more preferred. That is, it is more preferred that in structural formula (3-2) or (3-3), r or s be 1 or more with the R8 or R9, or at least one of the R8s or R9s, being hydroxy or alkoxy. Hydroxybenzaldehyde compounds represented by structural formula (3-2) in which r is 1 or more with the R8, or at least one of the R8s, being hydroxyl are also preferred. With such a hydroxybenzaldehyde compound, the phenolic hydroxyl-containing compound forms efficiently. It is more preferred that the aldehyde be any of 4-hydroxy-3-methoxybenzaldehyde, 3-ethoxy-4-hydroxybenzaldehyde, salicylaldehyde, 3-hydroxybenzaldehyde, 4-hydroxybenzaldehyde, and 2,4-dihydroxybenzaldehyde, any of salicylaldehyde, 3-hydroxybenzaldehyde, and 4-hydroxybenzaldehyde in particular.

The basic catalyst used in method 1 can be, for example, an alkali metal hydroxide, such as sodium hydroxide, lithium hydroxide, or potassium hydroxide, or an alkaline earth metal hydroxide, such as calcium hydroxide. It is particularly preferred that the basic catalyst be an alkali metal hydroxide because of its catalytic potential higher than that of alkaline earth metal hydroxides. The amount of the basic catalyst is preferably between 0.02 and 1.00 mole per mole based on the total number of moles of the dihydroxynaphthalene and the naphthol.

The acid catalyst used in method 2 can be, for example, an inorganic acid, such as hydrochloric acid, sulfuric acid, or phosphoric acid, an organic acid, such as methanesulfonic acid, p-toluenesulfonic acid, or oxalic acid, or a Lewis acid, such as boron trifluoride, anhydrous aluminum chloride, or zinc chloride. The amount of the acid catalyst is preferably between 0.1% and 25% by mass based on the total mass of the reactants.

In process 1, the proportion of the dihydroxynaphthalene and the naphthol to formaldehyde in the reaction is preferably, as a molar ratio [(total molar amount of the dihydroxynaphthalene and naphthol)/(molar amount of formaldehyde)], between 0.1 and 3.0. This ensures the phenolic hydroxyl-containing compound forms efficiently.

In process 1, the temperature at which the dihydroxynaphthalene and the naphthol are reacted with formaldehyde is preferably between 50° C. and 100° C. At these temperatures, the phenolic hydroxyl-containing compound forms efficiently.

In process 1, the reaction of the dihydroxynaphthalene and the naphthol with formaldehyde may optionally be carried out in an organic solvent. Examples of organic solvents used include alcohol solvents such as propanol, butanol, ethylene glycol, glycerol, ethylene glycol monomethyl ether, ethylene glycol monoethyl ether, ethylene glycol monobutyl ether, and propylene glycol monomethyl ether and ester solvents such as butyl acetate, ethylene glycol monomethyl ether acetate, ethylene glycol monoethyl ether acetate, and propylene glycol monomethyl ether acetate.

In process 1, the reaction of the dihydroxynaphthalene and the naphthol with formaldehyde is followed by neutralization of the system with an acidic compound. The neutralized system is cooled, and the resulting crystals of the composition are filtered out. The crystals are washed with water and dried, giving a phenolic resin composition that contains the phenolic hydroxyl-containing compound. The phenolic hydroxyl-containing compound can be obtained with a higher purity by, for example, dissolving the phenolic resin once again, in one of the aforementioned alcohol solvents or any other solvent, and adding the resulting solution dropwise to water for reprecipitation.

In method 2, the proportion of the dihydroxynaphthalene and the naphthol to the aldehyde in the reaction is preferably, as a molar ratio [(total molar amount of the dihydroxynaphthalene and naphthol)/(molar amount of the aldehyde)], between 0.1 and 3.0. This ensures the phenolic hydroxyl-containing compound forms efficiently.

The temperature at which the dihydroxynaphthalene compound is reacted with the aldehyde compound is preferably between 50° C. and 120° C. At these temperatures, the phenolic hydroxyl-containing compound forms efficiently.

In method 2, the reaction of the dihydroxynaphthalene and the naphthol with the aldehyde may optionally be carried out in an organic solvent. The organic solvent can be, for example, any of those organic solvents that can be used in process 1.

In method 2, the reaction of the dihydroxynaphthalene and the naphthol with the aldehyde is followed by water washing of the reaction mixture. The washed mixture is dried by removing the organic solvent, with heating under reduced pressure for example, giving a phenolic resin composition that contains the phenolic hydroxyl-containing compound. The phenolic hydroxyl-containing compound can be obtained with a higher purity by, for example, dissolving the phenolic resin once again, in one of the aforementioned alcohol solvents or any other solvent, and adding the resulting solution dropwise to water for reprecipitation.

In processes 1 and 2, the amounts of the dihydroxynaphthalene and the naphthol are preferably, as a molar ratio (dihydroxynaphthalene:naphthol), between 1:0.5 and 1:2.0, more preferably 1:0.7 and 1:1.5, by reason of the coating properties and heat resistance of the resulting compound when used as a resist material.

Such phenolic hydroxyl-containing compounds according to the present invention, highly soluble in commonly used organic solvents and superior in thermal decomposition resistance as described above, can be used in various electrical and electronic component applications such as adhesives, paints, photoresists, and printed circuit boards. With their superior alkali solubility, the phenolic hydroxyl-containing compounds according to the present invention are particularly suitable for use in resist applications and provide resist materials superior in light sensitivity and resolution. Furthermore, bottom resist films made using a phenolic hydroxyl-containing compound according to the present invention exhibit superior dry-etch and thermal decomposition resistance and low optical reflection. In addition, the phenolic hydroxyl-containing compounds according to the present invention can potentially be applied to, for example, qualitative or quantitative analysis of metal ions, separation of metal ions, molecular sensors, artificial enzymes, materials for different chromatographic techniques, and charge controlling agents for toners, by virtue of their clathrating and catalytic functions derived from the calixarene structure.

A photosensitive composition according to the present invention contains, as essential components, a phenolic hydroxyl-containing compound according to the present invention [hereinafter abbreviated to "the phenolic hydroxyl-containing compound (A)"] and a photosensitizer (B1).

The photosensitizer (B1) used in the present invention can be, for example, a quinonediazide-bearing compound. Specific examples of quinonediazide-bearing compounds include complete esters, partial esters, amides, and partial amides of aromatic (poly)hydroxy compounds with quinonediazide-bearing sulfonic acids, such as naphthoquinone-1,2-diazide-5-sulfonic acid, naphthoquinone-1,2-diazide-4-sulfonic acid, and ortho-anthraquinone diazide sulfonic acid.

Examples of aromatic (poly)hydroxy compounds used include polyhydroxybenzophenone compounds such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, and 2,3,3',4,4',5'-hexahydroxybenzophenone;

bis[(poly)hydroxyphenyl]alkane compounds such as bis(2,4-dihydroxyphenyl)methane, bis(2,3,4-trihydroxyphenyl)methane, 2-(4-hydroxyphenyl)-2-(4'-hydroxyphenyl)propane, 2-(2,4-dihydroxyphenyl)-2-(2',4'-dihydroxyphenyl)propane, 2-(2,3,4-trihydroxyphenyl)-2-(2',3',4'-trihydroxyphenyl)propane, 4,4'-(1-[4-{2-(4-hydroxyphenyl)-2-propyl}phenyl]ethylidene)bisphenol, and 3,3'-dimethyl-(1-[4-{2-(3-methyl-4-hydroxyphenyl)-2-propyl}phenyl]ethylidene)bisphenol;

tris(hydroxyphenyl)methane compounds such as tris(4-hydroxyphenyl)methane, bis(4-hydroxy-3,5-dimethylphenyl)-4-hydroxyphenylmethane, bis(4-hydroxy-2,5-dimethylphenyl)-4-hydroxyphenylmethane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-2,5-dimethylphenyl)-3,4-dihydroxyphenylmethane, and bis(4-hydroxy-3,5-dimethylphenyl)-3,4-dihydroxyphenylmethane and their methyl-substituted derivatives; and bis(cyclohexylhydroxyphenyl)(hydroxyphenyl)methane compounds such as bis(3-cyclohexyl-4-hydroxyphenyl)-3-hydroxyphenylmethane, bis(3-cyclohexyl-4-hydroxyphenyl)-2-hydroxyphenylmethane, bis(3-cyclohexyl-4-hydroxyphenyl)-4-hydroxyphenylmethane, bis(5-cyclohexyl-4-hydroxy-2-methylphenyl)-2-hydroxyphenylmethane, bis (5-cyclohexyl-4-hydroxy-2-methylphenyl)-3-hydroxyphenylmethane, bis(5-cyclohexyl-4-hydroxy-2-methylphenyl)-4-hydroxyphenylmethane, bis(3-cyclohexyl-2-hydroxyphenyl)-3-hydroxyphenylmethane, bis(5-cyclohexyl-4-hydroxy-3-methylphenyl)-4-hydroxyphenylmethane, bis(5-cyclohexyl-4-hydroxy-3-methylphenyl)-3-hydroxyphenylmethane, bis(5-cyclohexyl-4-hydroxy-3-methylphenyl)-2-hydroxyphenylmethane, bis(3-cyclohexyl-2-hydroxyphenyl)-4-hydroxyphenylmethane, bis(3-cyclohexyl-2-hydroxyphenyl)-2-hydroxyphenylmethane, bis(5-cyclohexyl-2-hydroxy-4-methylphenyl)-2-hydroxyphenylmethane, and bis(5-cyclohexyl-2-hydroxy-4-methylphenyl)-4-hydroxyphenylmethane and their methyl-substituted derivatives. These photosensitizers may be used individually or in combinations of two or more.

The amount of the photosensitizer(s) (B) in the photosensitive composition according to the present invention is preferably such that the photosensitizer(s) constitutes 5 to 50 parts by mass per 100 parts by mass of the phenolic hydroxyl-containing compound (A). This makes the composition superior in light sensitivity.

The photosensitive composition according to the present invention may contain any other resin (A') in combination with the phenolic hydroxyl-containing compound (A). The optional resin (A') can be any resin that is soluble in alkali developers by itself or dissolves in alkali developers when used in combination with additives such as an acid generator.

The optional resin (A') can be, for example, (A'-1) any phenolic resin other than the phenolic hydroxyl-containing compound (A); (A'-2) a homopolymers or copolymer of p-hydroxystyrene, p-(1,1,1,3,3,3-hexafluoro-2-hydroxypropyl)styrene or any other hydroxy-containing styrene; (A'-3) a derivative resulting from altering the hydroxyl groups of (A'-1) or (A'-2) with t-butoxycarbonyl, benzyloxycarbonyl, or any other acid-decomposing group; (A'-4) a homopolymers or copolymer of (meth)acrylic acid; or (A'-5) an alternating copolymer of an alicyclic polymerizable monomer, such as a norbornene or tetracyclodecene compound, with maleic anhydride or male imide.

Examples of optional phenolic resins (A'-1) include phenolic resins such as phenol novolac resins, cresol novolac resins, naphthol novolac resins, co-condensed novolac resins made from several phenolic compounds, phenolic resins modified with aromatic hydrocarbon formaldehyde resins, resins of dicyclopentadiene phenol adduct type, phenol aralkyl resins (Xylok resins), naphthol aralkyl resins, trimethylolmethane resins, tetraphenylolethane resins, biphenyl-modified phenolic resins (polyphenolic compounds in which bis-methylene group(s) connects phenolic nuclei), biphenyl-modified naphthol resins (polynaphthol compounds in which bis-methylene group(s) connects phenolic nuclei), aminotriazine-modified phenolic resins (polyphenolic compounds in which melamine, benzoguanamine, or any similar species connects phenolic nuclei), and novolac resins modified with alkoxy-containing aromatic rings (polyphenolic compounds in which formaldehyde connects phenolic nuclei and alkoxy-containing aromatic rings).

Of these optional phenolic resins (A'), cresol novolac resins and co-condensed novolac resins made from cresol and other phenolic compounds are particularly preferred. These resins make the photosensitive resin composition highly sensitive and superior in heat resistance. The cresol novolac resins and co-condensed novolac resins made from cresol and other phenolic compounds are, specifically, novolac resins made essentially from at least one cresol selected from the group consisting of o-cresol, m-cresol, and p-cresol and an aldehyde, optionally with other phenolic compounds.

Examples of optional, or non-cresol, phenolic compounds include phenol; xylenols such as 2,3-xylenol, 2,4-xylenol, 2,5-xylenol, 2,6-xylenol, 3,4-xylenol, and 3,5-xylenol; ethylphenols such as o-ethylphenol, m-ethylphenol, and p-ethylphenol; butylphenols such as isopropylphenol, butylphenol, and p-t-butylphenol; alkylphenols such as p-pentylphenol, p-octylphenol, p-nonylphenol, and p-cumylphenol; halogenated phenols such as fluorophenol, chlorophenol, bromophenol, and iodophenol; monosubstituted phenols such as p-phenylphenol, aminophenol, nitrophenol, dinitrophenol, and trinitrophenol; fused polycyclic phenols such as 1-naphthol and 2-naphthol; and polyphenols such as resorcinol, alkylresorcinols, pyrogallol, catechol, alkylcatechols, hydroquinone, alkylhydroquinones, phloroglucinol, bisphenol A, bisphenol F, bisphenol S, and dihydroxynaphthalene. These optional phenolic compounds may be used individually or in combinations of two or more. When optional phenolic compound(s) is used, the amount thereof is preferably between 0.05 and 1 mole per mole based on the total number of moles of the starting cresol(s).

Examples of aldehydes include formaldehyde, paraformaldehyde, trioxane, acetaldehyde, propionaldehyde, polyoxymethylene, chloral, hexamethylenetetramine, furfural, glyoxal, n-butyraldehyde, caproaldehyde, allylaldehyde, benzaldehyde, crotonaldehyde, acrolein, tetraoxymethylene, phenylacetaldehyde, o-tolualdehyde, and salicylaldehyde. These aldehydes may be used individually or in combinations of two or more. Formaldehyde is particularly preferred because of its superior reactivity and can be used in combination with other aldehyde compounds. If formaldehyde is used in combination with any other aldehyde compound, it is preferred that the amount of the additional aldehyde be between 0.05 and 1 mole per mole of formaldehyde.

In producing the novolac resin, the ratio of aldehydes to phenolic compounds in the reaction is preferably in the range of 0.3 to 1.6 moles, more preferably 0.5 to 1.3, of aldehydes per mole of phenolic compounds. This makes the photosensitive resin composition superior in sensitivity and heat resistance.

In an exemplary method, the phenolic compound is reacted with the aldehyde at a temperature of 60° C. to 140° C. in the presence of an acid catalyst, and then water and any residual monomers are removed under reduced pressure. Examples of acid catalysts used include oxalic acid, sulfuric acid, hydrochloric acid, phenolsulfonic acid, para-toluene sulfonic acid, zinc acetate, and manganese acetate. These acid catalysts may be used individually or in combinations of two or more. Oxalic acid is particularly preferred because of its superior catalytic activity.

Of such cresol novolac resins and co-condensed novolac resins made from cresol and other phenolic compounds, particularly preferred cresol novolac resins are made using meta-cresol alone or meta-cresol and para-cresol in combination. For the latter, the molar ratio between meta-cresol and para-cresol in the reaction [meta-cresol/para-cresol] is preferably between 10/0 and 2/8, more preferably between 7/3 and 2/8. This leads to a good balance between the sensitivity and heat resistance of the photosensitive resin composition.

When an optional resin (A') is used, the proportions of the phenolic hydroxyl-containing compound (A) and the optional resin (A') can be adjusted according to the intended purpose of use. For example, because of the superior light sensitivity, resolution, and heat resistance the phenolic hydroxyl-containing compound (A) exhibits when used in combination with a photosensitizer (B1), photosensitive compositions based on the compound (A) are ideal for resist applications. The proportion of the phenolic hydroxyl-containing compound (A) to the total amount of resin components is preferably 60% by mass or more, more preferably 80% by mass or more. This makes the curable composition highly sensitive to light and superior in resolution and heat resistance.

By virtue of its superior light sensitivity, furthermore, the phenolic hydroxyl-containing compound (A) can also be used as a sensitivity improver. In this case, the proportions of the phenolic hydroxyl-containing compound (A) and the optional resin (A') are preferably such that the phenolic hydroxyl-containing compound (A) constitutes 3 to 80 parts by mass per 100 parts by mass of the optional resin (A').

When an optional resin (A') is used, the amount of the photosensitizer(s) (B1) in the photosensitive composition according to the present invention is preferably such that the photosensitizer(s) constitutes 5 to 50 parts by mass per 100 parts by mass based on the total amount of resin components in the composition. This makes the photosensitive composition superior in light sensitivity.

The photosensitive composition according to the present invention may contain a surfactant for purposes such as improved film formation properties, better pattern adhesion, and reduced occurrence of development defects in resist applications. Examples of surfactants used include nonionic surfactants, e.g., polyoxyethylene alkyl ether compounds such as polyoxyethylene lauryl ether, polyoxyethylene stearyl ether, polyoxyethylene cetyl ether, and polyoxyethylene oleyl ether, polyoxyethylene alkylallyl ethers such as polyoxyethylene octylphenol ether and polyoxyethylene nonylphenol ether, polyoxyethylene-polyoxypropylene block copolymers, sorbitan fatty acid ester compounds such as sorbitan monolaurate, sorbitan monopalmitate, sorbitan monostearate, sorbitan monooleate, sorbitan trioleate, and sorbitan tristearate, and polyoxyethylene sorbitan fatty acid ester compounds such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorosurfactants, i.e., surfactants that have fluorine atoms in their molecular structure, such as copolymers of fluoroaliphatic-bearing polymerizable monomers with [poly(oxyalkylene)] (meth)acrylate; and silicone surfactants, i.e., surfactants that have a silicone structural portion in their molecular structure. These may be used individually or in combinations of two or more.

The amount of the surfactant(s) is preferably between 0.001 and 2 parts by mass per 100 parts by mass of solid resin in the photosensitive composition according to the present invention.

In photoresist applications, the photosensitive composition according to the present invention can be made into a composition for resists by dissolving the phenolic hydroxyl-containing compound (A) and photosensitizer(s) (B1) in an organic solvent optionally with other resins (A') and/or additives such as surfactants, dyes, fillers, crosslinking agents, and dissolution aids. This can be directly used as a positive resist film, and a dried film of the composition for resists can be used as a positive resist film. The support film for the resist film can be a polyethylene, polypropylene, polycarbonate, polyethylene terephthalate, or other synthetic resin film. Both a single-layer film and multiple multilayer films can be used. The support film may have a surface treated by corona discharge or coated with a release agent.

Examples of organic solvents used in the composition according to the present invention for resists include, but are not limited to, alkylene glycol monoalkyl ethers such as ethylene glycol monomethyl ether, ethylene glycol monoethyl ether, ethylene glycol monopropyl ether, ethylene glycol monobutyl ether propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; alkylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate. These may be used individually or in combinations of two or more.

The composition according to the present invention for resists can be conditioned by combining its components, described above, and mixing them using, for example, a mixer. If the resin composition for photoresists contains fillers and/or pigments, it can be conditioned through dispersion or mixing using a dispersing machine, such as a dissolver, a homogenizer, or a three-roll mill.

In an exemplary photolithographic process that uses a composition according to the present invention for resists, the composition for resists is applied to the subject of the photolithography a silicon substrate and prebaked at a temperature of 60° C. to 150° C. Any coating technique can be used, such as spin coating, roll coating, flow coating, dip coating, spray coating, and doctor blading. A resist pattern is then created. Since the composition according to the present invention for resists is positive working, the desired resist pattern is exposed to light through a predetermined mask, and an alkali developer is applied to dissolve the exposed parts, forming the resist pattern. By virtue of its high alkali solubility in exposed parts and high alkali resistance in unexposed parts, the composition according to the present invention for resists can be formed into resist patterns superior in resolution.

The curable composition according to the present invention can be suitably used in bottom resist film and permanent resist film applications, and cured articles made by curing a curable composition according to the present invention are useful as bottom resist films and permanent resist films. A curable composition according to the present invention, specifically, contains a phenolic hydroxyl-containing compound (A) according to the present invention and a curing agent (B2) as essential components.

The curing agent (B2) used in the present invention can be, for example, a melamine, guanamine, glycoluril, or urea compound substituted with at least one group selected from methylol, alkoxymethyl, and acyloxymethyl, a resol resin, an epoxy compound, an isocyanate compound, an azide compound, a compound with an alkenyl-ether or other double bond, an acid anhydride, or an oxazoline compound.

Examples of melamine compounds include hexamethylolmelamine, hexamethoxymethylmelamine, hexamethylolmelamine compounds with 1 to 6 methylol groups methoxymethylated, hexamethoxyethylmelamine, hexaacyloxymethylmelamines, and hexamethylolmelamine compounds with 1 to 6 methylol groups acyloxymethylated.

Examples of guanamine compounds include tetramethylolguanamine, tetramethoxymethylguanamine, tetramethoxymethylbenzoguanamine, tetramethylolguanamine compounds with 1 to 4 methylol groups methoxymethylated, tetramethoxyethylguanamine, tetraacyloxyguanamines, and tetramethylolguanamine compounds with 1 to 4 methylol groups acyloxymethylated.

Examples of glycoluril compounds include 1,3,4,6-tetrakis(methoxymethyl)glycoluril, 1,3,4,6-tetrakis(butoxymethyl)glycoluril, and 1,3,4,6-tetrakis(hydroxymethyl)glycoluril.

Examples of urea compounds include 1,3-bis(hydroxymethyl)urea, 1,1,3,3-tetrakis(butoxymethyl)urea, and 1,1,3,3-tetrakis(methoxymethyl)urea.

Examples of resol resins include polymers resulting from an alkali-catalyzed reaction between a phenolic hydroxyl-containing compound, e.g., phenol, an alkyl phenol such as cresol or xylenol, phenylphenol, resorcinol, biphenyl, a bisphenol such as bisphenol A or bisphenol F, naphthol, or dihydroxynaphthalene, and an aldehyde compound.

Examples of epoxy compounds include tris(2,3-epoxypropyl)isocyanurate, trimethylolmethane triglycidyl ether, trimethylolpropane triglycidyl ether, and triethylolethane triglycidyl ether.

Examples of isocyanate compounds include tolylene diisocyanate, diphenylmethane diisocyanate, hexamethylene diisocyanate, and cyclohexane diisocyanate.

Examples of azide compounds include 1,1'-biphenyl-4,4'-bisazide, 4,4'-methylidenebisazide, and 4,4'-oxybisazide.

Examples of compounds with alkenyl-ether or other double bonds include ethylene glycol divinyl ether, triethylene glycol divinyl ether, 1,2-propanediol divinyl ether, 1,4-butanediol divinyl ether, tetramethylene glycol divinyl ether, neopentylglycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

Examples of acid anhydrides include aromatic acid anhydrides such as phthalic anhydride, trimellitic anhydride, pyromellitic anhydride, 3,3',4,4'-benzophenonetetracarboxylic dianhydride, biphenyltetracarboxylic dianhydride, 4,4'-(isopropylidene)diphthalic anhydride, and 4,4'-(hexafluoroisopropylidene)diphthalic anhydride; and alicyclic carboxylic anhydrides such as tetrahydrophthalic anhydride, methyltetrahydrophthalic anhydride, hexahydrophthalic anhydride, methylhexahydrophthalic anhydride, endomethylenetetrahydrophthalic anhydride dodecenylsuccinic anhydride, and trialkyltetrahydrophthalic anhydrides.

Of these, glycoluril compounds, urea compounds, and resol resins are particularly preferred. With these highly effective curing agents, bottom resist films formed from the composition will demonstrate superior dry-etch and thermal decomposition resistance. In particular, glycoluril compounds are preferred.

The amount of the curing agent (B2) in the curable composition according to the present invention is preferably such that the curing agent constitutes 0.5 to 20 parts by mass per 100 parts by mass of the phenolic hydroxyl-containing compound (A). This makes the composition superior in curability.

The curable composition according to the present invention may contain any other resin in combination with the phenolic hydroxyl-containing compound (A). Examples of optional resins used include novolac resins, resins resulting from addition polymerization of an alicyclic diene compound, such as dicyclopentadiene, with a phenolic compound, modified novolac resins made from a phenolic hydroxyl-containing compound and an alkoxy-containing aromatic compound, phenol aralkyl resins (Xylok resins), naphthol aralkyl resins, trimethylolmethane resins, tetraphenylolethane resins, biphenyl-modified phenolic resins, biphenyl-modified naphthol resins, aminotriazine-modified phenolic resins, and vinyl polymers.

More specific examples of novolac resins include polymers resulting from an acid-catalyzed reaction between a phenolic hydroxyl-containing compound, e.g., phenolenol, an alkyl phenol such as cresol or xylenol, phenylphenol, resorcinol, biphenyl, a bisphenol such as bisphenol A or bisphenol F, naphthol, or dihydroxynaphthalene and an aldehyde compound.

Examples of vinyl polymers include homopolymers and copolymers of vinyl compounds such as polyhydroxystyrene, polystyrene, polyvinyl naphthalene, polyvinyl anthracene, polyvinyl carbazole, polyindene, polyacenaphthylene, polynorbornene, polycyclodecene, polytetracyclododecene, polynortricyclene, and poly(meta)acrylate.

When an optional resin is used, the proportions of the phenolic hydroxyl-containing compound (A) and the optional resin can be adjusted according to the intended purpose of use. Preferably, the proportions are such that the optional resin constitutes 0.5 to 100 parts by mass per 100 parts by mass of the phenolic hydroxyl-containing compound (A). This makes the advantages of the present invention of superior resistance to dry etching and thermal decomposition more significant.

When an optional resin is used, furthermore, the amount of the curing agent (B2) in the curable composition according to the present invention is preferably such that the curing agent constitutes 0.5 to 50 parts by mass per 100 parts by mass based on the total amount the phenolic hydroxyl-containing compound (A) and the optional resin. This makes the composition superior in curability.

In bottom resist film (BARC film) or permanent resist film applications, the curable composition according to the present invention can be made into a composition for bottom resist films or composition for permanent resist films by dissolving the phenolic hydroxyl-containing compound (A) and a curing agent (B) in an organic solvent optionally with other resins and/or additives such as surfactants, dyes, fillers, crosslinking agents, and dissolution aids.

Examples of organic solvents include, but are not limited to, alkylene glycol monoalkyl ethers such as ethylene glycol monomethyl ether, ethylene glycol monoethyl ether, ethylene glycol monopropyl ether, ethylene glycol monobutyl ether propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; alkylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate. These may be used individually or in combinations of two or more.

The composition according to the present invention for bottom resist films and that for permanent resist films can be conditioned by combining their components, described above, and mixing them using, for example, a mixer. If the composition according to the present invention for bottom resist films or permanent resist films contains fillers and/or pigments, it can be conditioned through dispersion or mixing using a dispersing machine, such as a dissolver, a homogenizer, or a three-roll mill.

In an exemplary process for creating a bottom resist film from a composition according to the present invention for bottom resist films, the composition for bottom resist films is first applied to the subject of the photolithography, such as a silicon substrate, and dried at a temperature of 100° C. to 200° C. The resulting coating is formed into a bottom resist film by, for example, curing with heating at a temperature of 250° C. to 400° C. Then, conventional photolithography is performed on this bottom film to form a resist pattern, and the film is dry-etched with, for example, a halogen plasma gas. In this way, a resist pattern is formed in accordance with the multilayer resist scheme. By virtue of their superior etch resistance and low optical reflection, coatings made from a curable composition according to the present invention can be suitably used in bottom resist film applications.

In an exemplary photolithographic process that uses a curable composition according to the present invention for permanent films, a solution or dispersion of the photosensitive composition for permanent films in an organic solvent is applied to the subject of the photolithography a silicon substrate and prebaked at a temperature of 60° C. to 150° C. Any coating technique can be used, such as spin coating, roll coating, flow coating, dip coating, spray coating, and doctor blading. A resist pattern is then created. When the photosensitive composition for permanent films is positive working, the desired resist pattern is exposed to light through a predetermined mask, and an alkali developer is applied to dissolve the exposed parts, forming the resist pattern. By virtue of its high light sensitivity, the photosensitive composition according to the present invention for permanent films can be formed into resist patterns superior in resolution.

Thin films made through the application of a curable composition according to the present invention for permanent films (coatings or permanent resist films) are suitable for use as permanent films, films that remain in finished products optionally with prior formation of resist patterns. Specific examples of permanent films related to semiconductor devices include solder resists, packaging material, underfill, package bonding layers for circuit devices or other components, and layers for bonding integrated circuit devices to a circuit board. Specific examples of permanent films related to thin displays, typified by LCDs and OELDs, include protective coatings for thin-film transistors, protective coatings for liquid-crystal color filters, black matrix, and spacers. Besides being superior in heat resistance and moisture absorption resistance, permanent films made from a photosensitive composition according to the present invention for permanent films offer the outstanding advantage of low contamination in particular, because they release only traces of hydroxynaphthalenes. Of particular importance is therefore that in producing display materials, the manufacturer can minimize the degradation of image quality associated with contamination, which is serious for display materials, by forming permanent films from a photosensitive composition according to the present invention for permanent films. The photosensitive composition according to the present invention for permanent films is therefore a material with little risk of image quality degradation that combines high sensitivity, high heat resistance, and hygroscopic reliability.

EXAMPLES

The following specifically describes the present invention by providing examples and comparative examples. In the examples and comparative examples, "parts" and "%" are by mass unless otherwise specified. The measurement conditions for GPC and FD-MS spectrometry were as follows.
<GPC Conditions>
Instrument: Tosoh Corporation "HLC-8220 GPC"
Columns: Tosoh Corporation "HHR-H" guard column (6.0 mm I.D.×4 cm)+Tosoh Corporation "TSK-GEL GMHHR-N" (7.8 mm I.D.×30 cm)+Tosoh Corporation "TSK-GEL GMHHR-N" (7.8 mm I.D.×30 cm)+Tosoh Corporation "TSK-GEL GMHHR-N" (7.8 mm I.D.×30 cm)+ Tosoh Corporation "TSK-GEL GMHHR-N" (7.8 mm I.D.× 30 cm)

Detector: ELSD (Alltech Japan K.K. "ELSD 2000")
Data processing: Tosoh Corporation "GPC-8020 Model II Data Analysis Version 4.30"
Measurement conditions: Column temperature 40° C.
Developing solvent Tetrahydrofuran (THF)
Flow rate 1.0 ml/min
Sample: A solution of 1.0% by mass resin, on a solid basis, in tetrahydrofuran filtered through a microfilter (5 µl)
Standard samples: As directed in the measurement manual for "GPC-8020 Model II Data Analysis Version 4.30," the below listed monodisperse polystyrenes, with known molecular weights, were used.
(Monodisperse Polystyrenes)
Tosoh Corporation "A-500"
Tosoh Corporation "A-1000"
Tosoh Corporation "A-2500"
Tosoh Corporation "A-5000"
Tosoh Corporation "F-1"
Tosoh Corporation "F-2"
Tosoh Corporation "F-4"
Tosoh Corporation "F-10"
Tosoh Corporation "F-20"
Tosoh Corporation "F-40"
Tosoh Corporation "F-80"
Tosoh Corporation "F-128"
Tosoh Corporation "F-288"
Tosoh Corporation "F-550"
<FD-MS Spectrometry Conditions>
Measurements were taken using JEOL Ltd. AX505H (FD505H) double-focusing mass spectrometer.

Example 1 [Synthesis of a Phenolic Hydroxyl-Containing Compound with a Molecular Structure of Structural Formula (1)]

Figure 2:
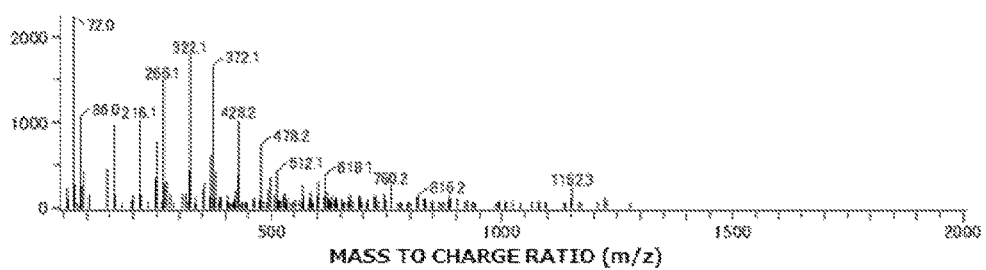
FIG. 2 is an FD-MS chart of phenolic hydroxyl-containing compound (1), obtained in Example 1.
Figure 3:
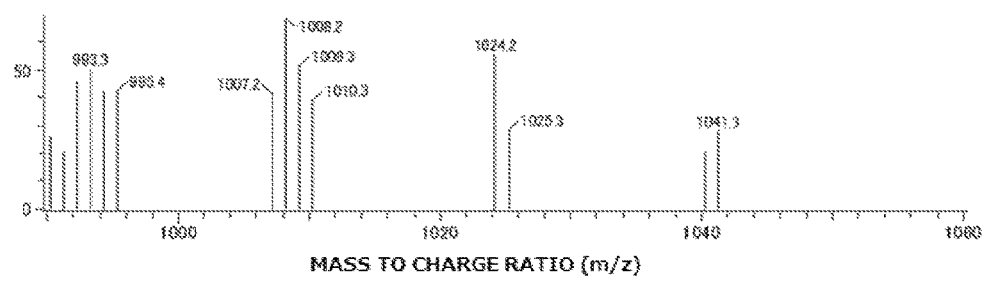
FIG. 3 is an FD-MS chart (enlarged to 32 times) of phenolic hydroxyl-containing compound (1), compound obtained in Example 1.

A flask fitted with a thermometer, a dropping funnel, a condenser, and a stirrer was charged with 120 g of 1,6-dihydroxynaphthalene, 36 g of 1-naphthol, 122 g of 4-hydroxybenzaldehyde, 290 g of 1-butanol, and 1.7 g of 95% sulfuric acid. After heating to 100° C., the ingredients were allowed to react with stirring for 12 hours. After the completion of the reaction, 160 g of ion-exchanged water was added. In a separatory funnel, the aqueous layer, which was the lower layer and had a pH of 1, was released. The organic layer was washed with 160 g of ion-exchanged water seven times, and the released aqueous layers were checked to ensure that the pH was 4. The organic layer, or the upper layer, was concentrated by heating under reduced pressure using an evaporator. The residue was dried, giving 246 g of a composition containing 74% compound (A1) based on area ratios in GPC. An FD-MS spectrum of the composition had peaks at 992, 1008, 1024, and 1041, which correspond to a cyclic compound of structural formula (1) [where p is 4], indicating that compound (A1), constituting 74% of the composition, was a phenolic hydroxyl-containing compound having a molecular structure represented by structural formula (1). In this example, compound (A1) clearly had a unit represented by structural formula (1-1) in combination with a unit represented by structural formula (1-2) because 1,6-dihydroxynaphthalene and 1-naphthol were used. FIGS. 1, 2, and 3 are GPC, FD-MS (full), and FD-MS (enlarged to 32 times) charts, respectively, of the phenolic hydroxyl-containing compound (A1).

Using the resulting phenolic hydroxyl-containing compound (A1)-based composition, the solubility in solvent and heat resistance of the phenolic hydroxyl-containing compound (A1) were evaluated as described below. The results are given in Table 1.

<Solubility in Solvent Testing>

Eight parts of the phenolic hydroxyl-containing compound (A1)-based composition and 2 parts of a photosensitizer (Toyo Gosei Co., Ltd. "P-200"; a condensation product of 1 mole of 4,4'-[1-[4-[1-(4-hydroxyphenyl)-1-methylethyl]phenyl]ethylidene]bisphenol and 2 moles of 1,2-naphthoquinone-2-diazide-5-sulfonyl chloride) were added to propylene glycol monomethyl ether acetate (hereinafter abbreviated to "PGMEA") to make the concentration of the solution 20%. The mixture was stirred using a shaker at ordinary temperature, giving a PGMEA solution. The solution was stirred, and the solvent in the vessel was visually inspected.

Dissolved: Uniform and transparent (○ in Table 1)
Not dissolved: Solids separated out or precipitated (× in Table 1)

<Heat Resistance Testing>

The thermal decomposition temperature was determined by heating the composition at a constant rate with weight loss monitoring using a thermogravimetry/differential thermal analyzer (TG/DTA) under the conditions specified below. The higher this temperature is, the more resistant to heat the composition is.

Instrument: Seiko Instruments Inc. TG/DTA 6200
Temperature range: RT to 400° C.
Heating rate: 10° C./min
Atmosphere: Nitrogen Example 2 (Same as Above)

Figure 4:
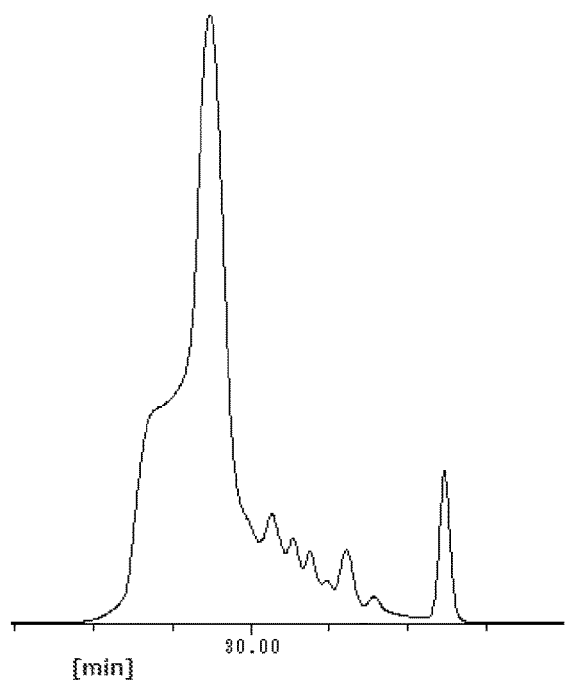
FIG. 4 is a GPC chart of phenolic hydroxyl-containing compound (2), obtained in Example 2.
Figure 5:
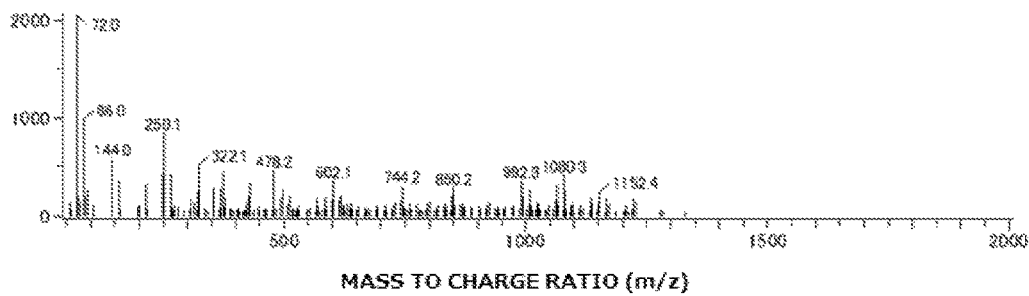
FIG. 5 is an FD-MS chart of phenolic hydroxyl-containing compound (2), obtained in Example 2.
Figure 6:
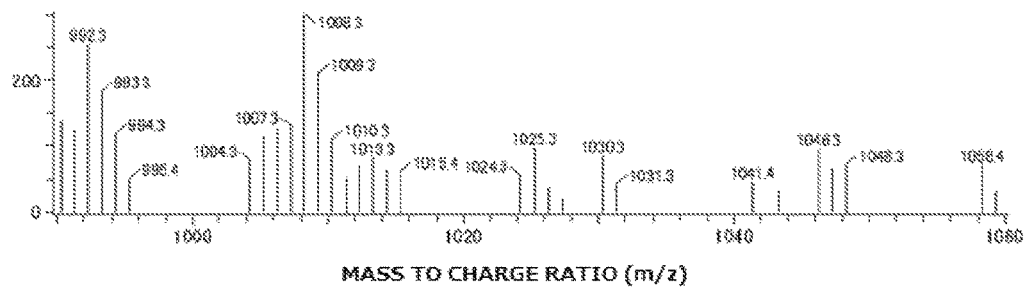
FIG. 6 is an FD-MS chart (enlarged to seven times) of phenolic hydroxyl-containing compound (2), obtained in Example 2.

The procedure of Example 1 was repeated with 80 g of 1,6-dihydroxynaphthalene and 72 g of 1-naphthol, yielding 237 g of a composition containing 79%, based on area ratios in GPC, of a phenolic hydroxyl-containing compound (A2) having a molecular structure of structural formula (1). An FD-MS spectrum of the composition had peaks at 992, 1008, 1024, 1041, and 1058, which correspond to a cyclic compound of structural formula (i), indicating that compound (A2), constituting 79% of the composition, was a phenolic hydroxyl-containing compound having a molecular structure represented by structural formula (1). FIGS. 4, 5, and 6 are GPC, FD-MS (full), and FD-MS (enlarged to seven times) charts, respectively, of the phenolic hydroxyl-containing compound (A2).

In the same way as in Example 1, the solubility in solvent and heat resistance of the phenolic hydroxyl-containing compound (A2) were evaluated. The results are given in Table 1.

Example 3 (Same as Above)

Figure 7:
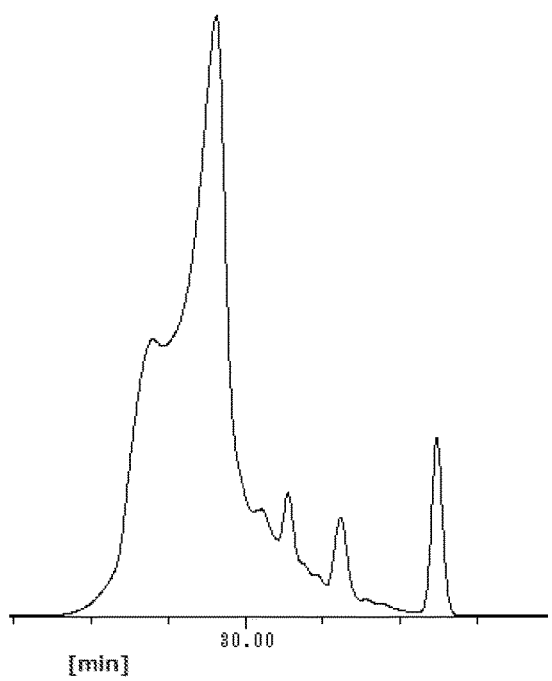
FIG. 7 is a GPC chart of phenolic hydroxyl-containing compound (3), obtained in Example 3.
Figure 8:
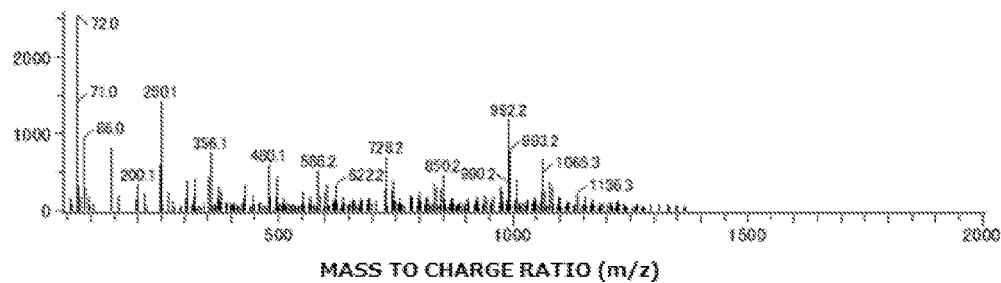
FIG. 8 is an FD-MS chart of phenolic hydroxyl-containing compound (3), obtained in Example 3.
Figure 9:
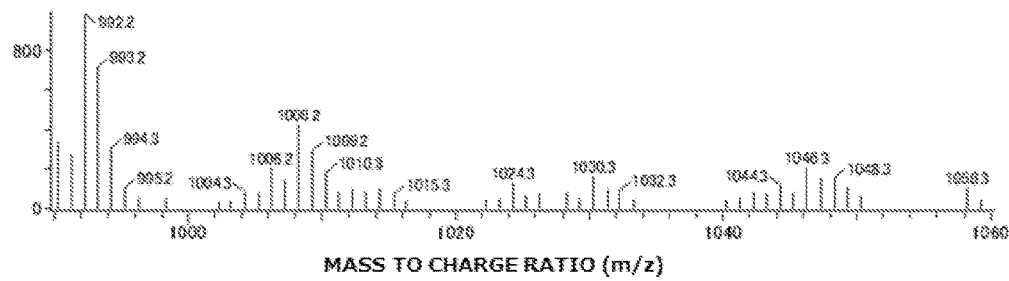
FIG. 9 is an FD-MS chart (enlarged to three times) of phenolic hydroxyl-containing compound (3), obtained in Example 3.

The procedure of Example 1 was repeated with 40 g of 1,6-dihydroxynaphthalene and 108 g of 1-naphthol, yielding 231 g of a composition containing 65%, based on area ratios in GPC, of a phenolic hydroxyl-containing compound (A3) having a molecular structure of structural formula (1). An FD-MS spectrum of the composition had peaks at 992, 1008, 1024, 1041, and 1058, which correspond to a cyclic compound of structural formula (i), indicating that compound (A3), constituting 65% of the composition, was a phenolic hydroxyl-containing compound having a molecular structure represented by structural formula (1). FIGS. 7, 8, and 9 are GPC, FD-MS (full), and FD-MS (enlarged to three times) charts, respectively, of the phenolic hydroxyl-containing compound (A3).

In the same way as in Example 1, the solubility in solvent and heat resistance of the phenolic hydroxyl-containing compound (A3) were evaluated. The results are given in Table 1.

Comparative Example 1 (Synthesis of a Comparative Noncyclic Compound)

A flask fitted with a thermometer, a condenser, and a stirrer was charged with 160 g (1.00 mole) of 1,6-dihydroxynaphthalene, 400 g of methyl isobutyl ketone, 96 g of water, and 27.7 g (0.85 moles) of 92% paraformaldehyde, and the ingredients were stirred at room temperature. To the mixture was added 4.8 g of an aqueous solution of para-toluene sulfonic acid adjusted to a concentration of 50%. The mixture was heated to 80° C. and allowed to react for 2 hours with stirring. After the completion of the reaction, the solution in the system was transferred to a separatory funnel, and the aqueous layer was separated from the organic layer and removed. After being washed with water until the washing water became neutral, the organic layer was heated under reduced pressure to remove solvents, yielding 162 g of a comparative noncyclic compound [a novolac phenolic resin (A'1)].

In the same way as in Example 1, the solubility in solvent and heat resistance of the novolac phenolic resin (A'1) were evaluated. The results are given in Table 1.

Comparative Example 2 (Synthesis of a Comparative Cyclic Compound)

A flask fitted with a thermometer, a dropping funnel, a condenser, and a stirrer was charged with 48 g (0.3 moles) of 1-naphthol, 26 g (0.36 moles) of a 42% aqueous solution of formaldehyde, 50 g of isopropyl alcohol, and 9.4 g (0.11 moles) of a 48% sodium hydroxide, and the ingredients were stirred with nitrogen purge at room temperature. After heating to 80° C., the mixture was stirred for 1 hour. After the completion of the reaction, the mixture was neutralized with 8 parts by mass of monosodium phosphate. The mixture was then cooled, and the resulting crystals were filtered out. The crystals were washed with 50 g of water three times and then dried by heating under reduced pressure, giving 47 g of a comparative cyclic compound [a comparative phenolic hydroxyl-containing compound (A'2)].

In the same way as in Example 1, the solubility in solvent and heat resistance of the comparative phenolic hydroxyl-containing compound (A'2) were evaluated. The results are given in Table 1.

TABLE 1

|  | Example 1 | Example 2 | Example 3 | Comparative Example 1 | Comparative Example 2 |
|---|---|---|---|---|---|
| Phenolic hydroxyl-containing compound or phenolic resin | (A1) | (A2) | (A3) | (A'1) | (A'2) |
| Solubility in solvent | ○ | ○ | ○ | ○ | X |
| Thermal decomposition temperature (° C.) | 184 | 182 | 181 | 151 | 177 |

Example 4 (Preparation of a Photosensitive Composition)

A photosensitive composition was prepared using the phenolic hydroxyl-containing compound (A1)-based composition as described below. The alkali developability and resolution of coatings made using this composition were evaluated. The following describes the method of preparation of the composition used and the alkali developability and resolution testing conducted.

<Preparation of the Photosensitive Composition>

The photosensitive composition was prepared assuming resist applications, positive photoresist applications in particular. The coatings of this composition were made assuming use as resist coatings, positive photoresist coatings in particular. For the coatings made using this composition, alkali developability and resolution were evaluated. The following describes the method of preparation of the photosensitive composition and testing methods used.

Sixteen parts of the composition containing 74%, based on area ratios in GPC, phenolic hydroxyl-containing compound (A1) was dissolved in 80 parts of PGMEA. A mixture of the resulting solution with 4 parts of a photosensitizer (Toyo Gosei Co., Ltd. "P-200") was filtered through a 0.2-μm membrane filter, yielding a photosensitive composition (a). Likewise, a solution of 20 parts of the composition containing 74%, based on area ratios in GPC, phenolic hydroxyl-containing compound (A1) in 80 parts of PGMEA was filtered through a 0.2-μm membrane filter, giving a photosensitizer-free composition (b).

<Alkali Developability Testing>

Compositions (a) and (b) were each applied to a silicon wafer 5 inches in diameter using a spin coater. The applied compositions were dried at 110° C. for 60 seconds, giving coatings (A) and (B), respectively, approximately 1 μm thick. Coatings (A) and (B) were immersed in an alkali solution (a 2.38% aqueous solution of tetramethylammonium hydroxide) for 60 seconds. After that, the thickness of the coatings was measured using a film thickness measurement instrument (Filmetrics "F-20"), and the alkali dissolution rate (ADR) was determined from the measurement. The results are given in Table 2. The lower the rate of dissolution in the alkali solution of coating (A) is and the higher the alkali dissolution rate of coating (B) is, the higher the light sensitivity of coatings made from the composition for resists is.

<Resolution Testing>

The photosensitive composition (a), containing a photosensitizer, was applied to a silicon wafer 5 inches in diameter using a spin coater. The applied composition was dried at 110° C. for 60 seconds, giving a coated silicon wafer. This coated silicon wafer was exposed to light at 100 mJ/cm² using Ushio Inc. Multilight (g-, h-, and i-lines) with a photomask on its coated surface. The exposed silicon wafer was immersed in an alkali solution (a 2.38% aqueous solution of tetramethylammonium hydroxide) for 60 seconds. The surface of the pattern was washed with purified water, and the wafer was spin-dried using a spin coater and then dried at 100° C. for 60 seconds. The resist pattern on the dried silicon wafer was observed under a laser microscope (Keyence Corporation "VK-8500") and rated for its condition against the criteria below. The results are given in Table 2.

○: Resolution was achieved with L/S=5 μm.
×: Resolution was not achieved with L/S=5 μm.

Examples 5 and 6 and Comparative Examples 3 and 4

Photosensitive compositions were obtained by repeating the procedure of Example 4 with the phenolic hydroxyl-containing compound or phenolic resin specified in Table 2. Using these photosensitive compositions, the alkali developability and resolution were evaluated. The results are given in Table 2.

TABLE 2

|  | Example 4 | Example 5 | Example 6 | Comparative Example 3 | Comparative Example 4 |
|---|---|---|---|---|---|
| Phenolic hydroxyl-containing compound or phenolic resin | (A1) | (A2) | (A3) | (A'1) | (A'2) |
| Alkali dissolution rate (nm/sec) of photosensitizer-containing coating (A) | 1.2 | 1 | 0.8 | 170 | — |
| Alkali dissolution rate (nm/sec) of photosensitizer-free coating (B) | >200 | >200 | >200 | >200 | — |
| Resolution | ○ | ○ | ○ | X | X |

Footnote to Table 2
—: Not measurable. Crystals formed during the coating process, making further coating impossible.

Example 7 (Preparation of a Curable Composition)

A curable composition was prepared using the phenolic hydroxyl-containing compound (A1)-based composition as described below. The alkali developability and dry-etch resistance of coatings made using this composition were evaluated. The following describes the method of preparation of the composition used and the alkali developability and dry-etch resistance testing conducted.

<Preparation of the Curable Composition>

The curable composition was prepared assuming bottom resist film and permanent resist film applications. The coatings of this composition were made assuming use as bottom resist films or permanent resist films. For the coatings made using this composition, alkali developability and dry-etch resistance were evaluated. The following describes the method of preparation of the curable composition and testing methods used.

<Preparation of the Curable Composition>

Sixteen parts of the composition containing 74%, based on area ratios in GPC, phenolic hydroxyl-containing compound (A1) and 3 parts of a crosslinking agent (Tokyo Chemical Industry Co., Ltd. "1,3,4,6-Tetrakis(methoxymethyl)glycoluril") were added to 100 parts of PGMEA. The ingredients were mixed and dissolved to give a solution. This solution was filtered through a 0.2-μm membrane filter, yielding a curable composition.

<Alkali Developability Testing>

The curable composition was applied to a silicon wafer 5 inches in diameter using a spin coater. The applied composition was dried at 110° C. for 60 seconds, giving a silicon wafer with a coating approximately 1 μm thick thereon. This coated silicon wafer was immersed in an alkali solution (a 2.38% aqueous solution of tetramethylammonium hydroxide) for 60 seconds. The thickness of the immersed coating was measured using a film thickness measurement instrument (Filmetrics "F-20"), and the alkali dissolution rate (ADR) was determined from the measurement. The results are given in Table 3. The higher the alkali dissolution rate is, the higher the developability, in alkali solutions, of coatings made from the curable composition is.

<Dry-Etch Resistance Testing>

The curable composition was applied to a silicon wafer 5 inches in diameter using a spin coater. The silicon wafer was then heated at 180° C. for 60 seconds on a hotplate at an oxygen concentration of 20% by volume. The wafer was further heated at 350° C. for 120 seconds, giving a silicon wafer with a coating 0.3 µm thick thereon. The formed coating was etched using an etching unit (Shinko Seiki "EXAM") under the conditions of $CF_4/Ar/O_2$ ($CF_4$, 40 mL/min; Ar, 20 mL/min; $O_2$, 5 mL/min; pressure, 20 Pa; RF power, 200 W; processing time, 40 seconds; temperature, 15° C.). The etching rate was calculated from measured thicknesses of the coating before and after the etching, and the etch resistance was evaluated using it. The evaluation criteria were as given below. The results are given in Table 3.

○: The etching rate is 150 nm/min or less.
×: The etching rate is more than 150 nm/min.

Examples 8 and 9 and Comparative Examples 5 and 6

Curable compositions were obtained by repeating the procedure of Example 4 with the phenolic hydroxyl-containing compound or phenolic resin specified in Table 2. Using these photosensitive compositions, the alkali developability and dry-etch resistance of coatings were evaluated. The results are given in Table 3.

TABLE 3

| | Example 7 | Example 8 | Example 9 | Comparative Example 5 | Comparative Example 6 |
|---|---|---|---|---|---|
| Phenolic hydroxyl-containing compound or phenolic resin | (A1) | (A2) | (A3) | (A'1) | (A'2) |
| Alkali dissolution rate (nm/sec) of uncured coating | >200 | >200 | >200 | >200 | — |
| Dry-etch resistance | ○ | ○ | ○ | ○ | X |

Footnote to Table 3
—: Not measurable. Crystals formed during the coating process, making further coating impossible.

The invention claimed is:

1. A method of producing a calix[2-10]arene compound, which comprises a step of reacting a substituted or unsubstituted 1,6-dihydroxynaphthalene compound and a substituted or unsubstituted 1-naphthol with an aliphatic aldehyde having two or more carbon atoms or an aromatic aldehyde in the presence of an inorganic acid catalyst,
wherein up to four of the hydrogens bonded directly to the naphthalene ring of 1,6-dihydroxynaphthalene and up to five of the hydrogens bonded directly to the naphthalene ring of naphthol are replaced with substituents selected from a group consisting of an alkyl group, an alkoxy group, an aryl group which may have a substituent, an aralkyl group which may have a substituent, or a halogen atom, and plural substituents may be the same as or different from each other;
the calix arene compound includes a structure comprising units of substituted or unsubstituted 1,6-dihydroxynaphthalene structure and substituted or unsubstituted 1-naphthol structure.

2. The method of producing a calix[2-10]arene compound according to claim 1, wherein a total number of repeats the units of substituted or unsubstituted 1,6-dihydroxynaphthalene structure and substituted or unsubstituted 1-naphthol structure in the calix[2-10]arene compound is an integer of 2 to 10.

3. The method of producing a calix[2-10]arene compound according to claim 2, wherein the reaction of a substituted or unsubstituted 1,6-dihydroxynaphthalene compound and a substituted or unsubstituted 1-naphthol with an aliphatic aldehyde having two or more carbon atoms or an aromatic aldehyde in the presence of an inorganic acid catalyst is carried out in an organic solvent, and the organic solvent is a butanol.

4. The method of producing a calix[2-10]arene compound according to claim 1, wherein the inorganic acid catalyst is selected from one of the groups consisting of hydrochloric acid, sulfonic acid, phosphoric acid.

5. The method of producing a calix[2-10]arene compound according to claim 4, wherein the reaction of a substituted or unsubstituted 1,6-dihydroxynaphthalene compound and a substituted or unsubstituted 1-naphthol with an aliphatic aldehyde having two or more carbon atoms or an aromatic aldehyde in the presence of an inorganic acid catalyst is carried out in an organic solvent, and the organic solvent is a butanol.

6. The method of producing a calix[2-10]arene compound according to claim 1, wherein the inorganic acid catalyst is sulfonic acid.

7. The method of producing a calix[2-10]arene compound according to claim 6, wherein the reaction of a substituted or unsubstituted 1,6-dihydroxynaphthalene compound and a substituted or unsubstituted 1-naphthol with an aliphatic aldehyde having two or more carbon atoms or an aromatic aldehyde in the presence of an inorganic acid catalyst is carried out in an organic solvent, and the organic solvent is a butanol.

8. The method of producing a calix[2-10]arene compound according to claim 1, wherein the inorganic acid catalyst is strong sulfonic acid.

9. The method of producing a calix[2-10]arene compound according to claim 8, wherein the reaction of a substituted or unsubstituted 1,6-dihydroxynaphthalene compound and a substituted or unsubstituted 1-naphthol with an aliphatic aldehyde having two or more carbon atoms or an aromatic aldehyde in the presence of an inorganic acid catalyst is carried out in an organic solvent, and the organic solvent is a butanol.

10. The method of producing a calix[2-10]arene compound according to claim 1, wherein the reaction of a substituted or unsubstituted 1,6-dihydroxynaphthalene compound and a substituted or unsubstituted 1-naphthol with an aliphatic aldehyde having two or more carbon atoms or an aromatic aldehyde in the presence of an inorganic acid catalyst is carried out in an organic solvent, and the organic solvent is butanol.

* * * * *